US008753407B2

(12) United States Patent
Nguyen

(10) Patent No.: US 8,753,407 B2
(45) Date of Patent: Jun. 17, 2014

(54) TEMPORARY PROTECTIVE GASTROINTESTINAL DEVICE

(75) Inventor: Ninh T. Nguyen, Huntington Beach, CA (US)

(73) Assignee: Endoshield, Inc., New Hope, PA (US)

( * ) Notice: Subject to any disclaimer, the term of this patent is extended or adjusted under 35 U.S.C. 154(b) by 133 days.

(21) Appl. No.: 13/154,342

(22) Filed: Jun. 6, 2011

(65) Prior Publication Data

US 2012/0116528 A1    May 10, 2012

Related U.S. Application Data

(60) Provisional application No. 61/351,549, filed on Jun. 4, 2010.

(51) Int. Cl.
*A61F 2/04*    (2013.01)
*A61F 2/06*    (2013.01)

(52) U.S. Cl.
USPC ....... 623/23.7; 623/1.13; 623/1.15; 623/1.16; 623/1.27; 623/23.64; 623/23.65; 623/23.66

(58) Field of Classification Search
USPC .............. 623/1.13–1.16, 1.24–1.36, 623/23.64–23.68, 23.7–23.71; 606/151–155, 8
See application file for complete search history.

(56) References Cited

U.S. PATENT DOCUMENTS

| 5,662,713 | A * | 9/1997 | Andersen et al. | 128/898 |
| 6,152,956 | A | 11/2000 | Pierce | |
| 7,547,321 | B2 * | 6/2009 | Silvestri et al. | 623/1.15 |
| 8,372,134 | B2 * | 2/2013 | Schlick et al. | 623/1.13 |
| 2006/0149137 | A1 | 7/2006 | Pingleton et al. | |
| 2006/0224226 | A1 * | 10/2006 | Huang et al. | 623/1.11 |
| 2008/0208314 | A1 | 8/2008 | Skerven | |
| 2010/0010519 | A1 | 1/2010 | Stopek et al. | |
| 2012/0150274 | A1 * | 6/2012 | Shalev et al. | 623/1.12 |

OTHER PUBLICATIONS

International Search Report from counterpart International Patent Application No. PCT/US2011/039334.

* cited by examiner

*Primary Examiner* — David Isabella
*Assistant Examiner* — Yashita Sharma
(74) *Attorney, Agent, or Firm* — Edwards Wildman Palmer LLP; Scott D. Wofsy; Christopher J. Cillié

(57) ABSTRACT

Disclosed is an intraluminal gastrointestinal (GI) device that is placed at the time of surgery to protect a freshly constructed GI anastomosis, GI staple-line, or the like. For the esophagus and stomach, the device covers the esophagus, stomach, and anastomosis/staple-line. For the pancreas or biliary duct, the device covers the biliary duct, pancreatic duct, and small bowel. For the colon and rectum, the device is a self expanding protective barrier that covers the anal canal, the anus, and the colon or rectum, approximately 18 cm proximal to the anus. These devices provide a waterproof barrier between the gastrointestinal content and the mucosa of the GI tract and the newly constructed anastomosis. Additionally, the design of the device is made to prevent migration within the gastrointestinal tract and facilitate removal of the device.

30 Claims, 13 Drawing Sheets

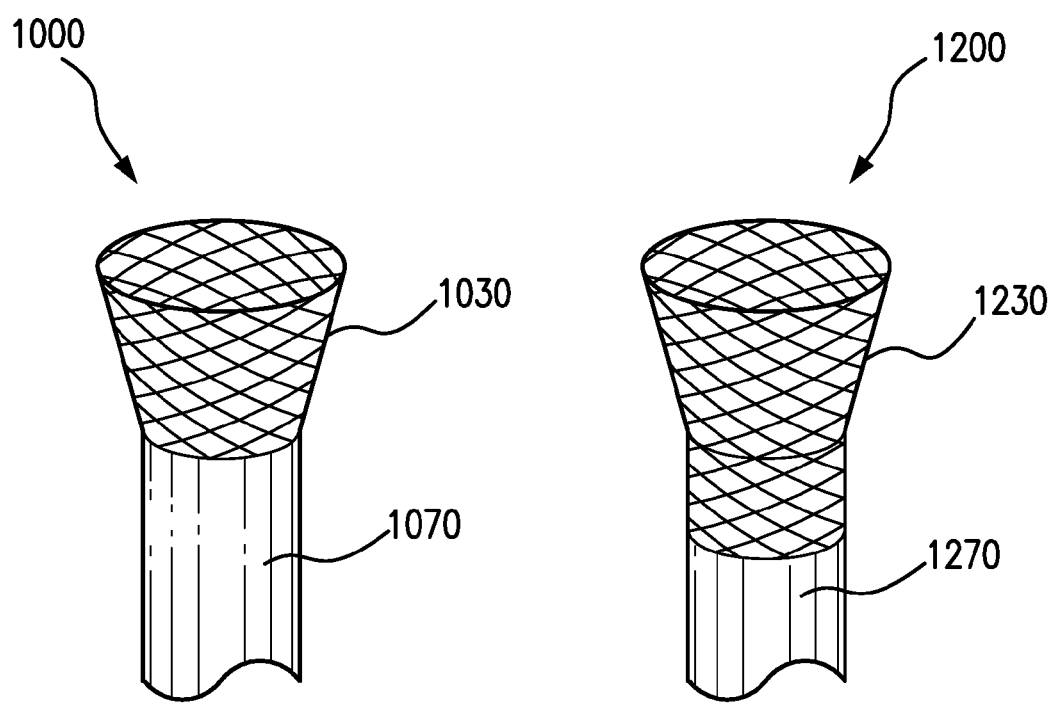

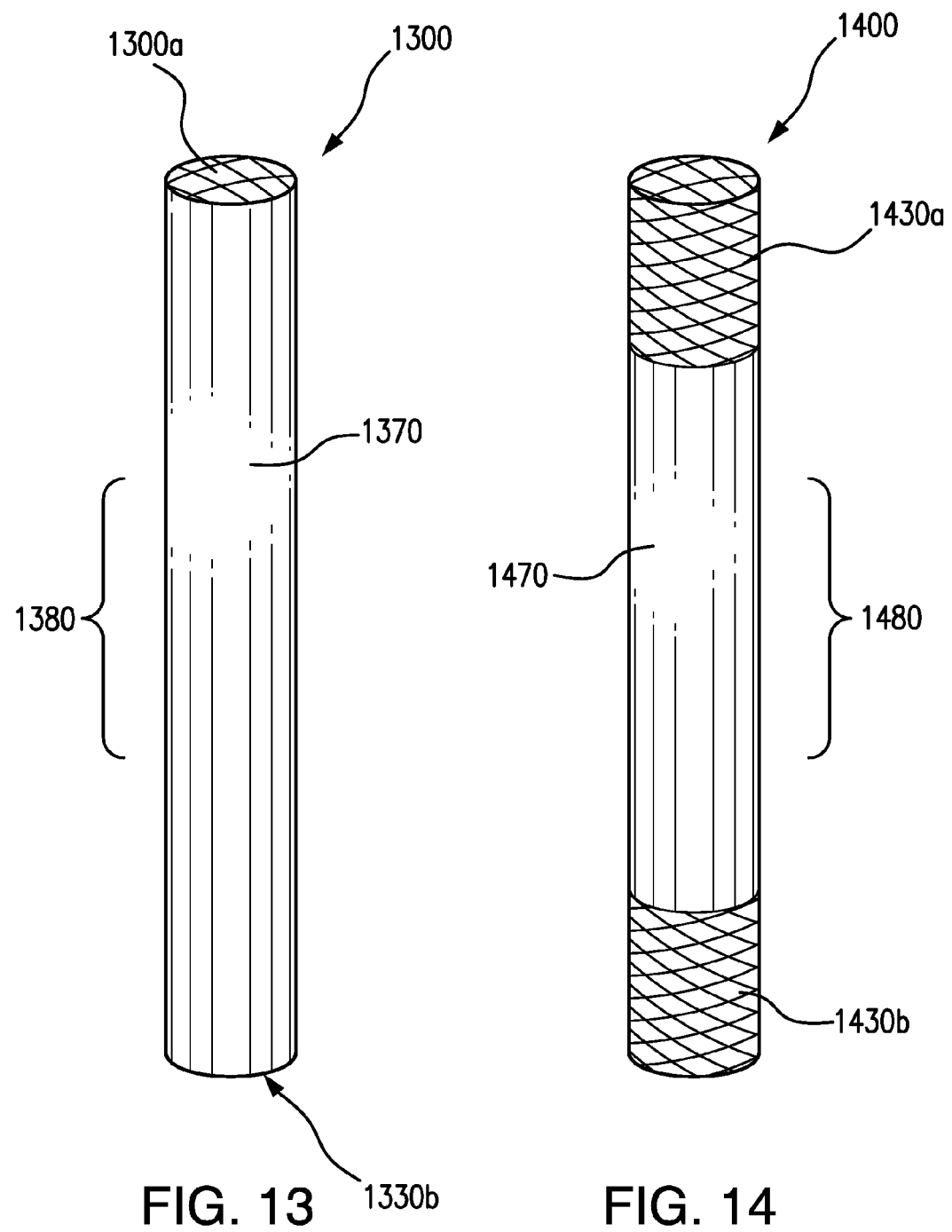

TEMPORARY PROTECTIVE GASTROINTESTINAL DEVICE

CROSS-REFERENCE TO RELATED APPLICATIONS

This application claims the benefit of U.S. Provisional Application No. 61/351,549, filed on Jun. 4, 2010, which is expressly incorporated herein in its entirety by reference thereto.

FIELD OF THE INVENTION

The present invention relates to the field of medical devices that reside within a lumen of the gastrointestinal tract, and more particularly to providing a platform for protection of a freshly constructed esophageal, gastric, pancreatic, colon or rectal anastomosis.

BACKGROUND

The number of gastrointestinal (GI) surgeries has been estimated at 500,000 cases annually in the US and the most dreaded complication after any GI surgery is an anastomotic leak or staple-line failure. In the upper GI tract, the main GI surgeries are the Roux-en-Y gastric bypass and sleeve gastrectomy for treatment of morbid obesity, esophagogastrectomy and gastrectomy for benign or malignant disease, and pancreaticoduodenectomy (Whipple) operation.

The number of gastric bypass, sleeve gastrectomy, esophagogastrectomy, gastrectomy, and Whipple operation in the US is estimated to be 200,000 cases per year. Leaks occur in 1-15% of cases depending on the type of operation. Treatments for leaks are complex including re-operation, drainage, long-term antibiotics, lengthy hospitalization, and are very costly for the healthcare system.

The number of colon and rectal surgeries has been estimated between 200,000-300,000 per year in the U.S. for treatment of both benign and malignant disease of the colon and rectum. Rectal and colon resections with a low anastomosis can be associated with high risk for anastomotic dehiscence, leaks, and intra-abdominal abscesses. Despite attention to technical details including construction of a tension-free anastomosis with good blood supply, anastomotic leaks after colon surgery can range between 3-5% and leaks after rectal surgery can range between 10-15% and associated with major morbidities and even mortality. Additionally, anastomotic leak after colon or rectal resection for cancer may be associated with a lower 5-year survival. Treatments for leaks are complex including re-operation, drainage, diversion of the intestine (if not done already), long-term antibiotics, lengthy hospitalization, and are very costly for the healthcare system.

In response to the high risk for anastomotic leaks after rectal surgery, most surgeons perform a prophylactic diverting ileostomy to divert the fecal stream away from the newly constructed rectal anastomosis; however, a diverting ileostomy can be associated with its own risk of morbidities. In addition, the ileostomy will need to be taken down by another operation several weeks after the primary operation which can also be associated with additional morbidity, in addition to the patient's discomfort and pain associated with a second surgery. At the current time, the only prophylactic method to minimize anastomotic leak is surgery by construction of a diverting ileostomy. Despite the use of a prophylactic ileostomy, the leak rate after rectal surgery has not reduced tremendously; however, the severity of the leaks has improved.

Currently, there are no FDA approved indications for prophylactic placement of a protective device after esophageal, gastric, colon and rectal, or pancreatic surgery and there are no available devices on the market. The currently available endoluminal stents on the market are indicated only for relief of obstruction from gastrointestinal malignancy. Therefore, these stents are not optimal in a setting where there are no obstructions and their configurations were not constructed specifically to best protect an anastomosis.

Such conventional methods and systems have generally been considered satisfactory for their intended purpose of treating obstructions within the GI tract. However, there is still a need in the art for a device that can be placed at the time of GI surgery to allow for improved reduction of complications and leaks that develop after colon, rectal, gastric, pancreatic, and esophageal surgeries while minimizing migration of the device through the lumen. There also remains a need in the art for such a prophylactic removable device that is easy to make and use. The present invention provides a solution for these problems.

SUMMARY

In accordance with example embodiments of the present invention, an intraluminal protective device configured to be secured in a lumen of a patient, includes: a proximal tubular stent having opposed proximal and distal end portions and expandable from a collapsed state to an expanded state to exert a first radial force against an interior of the lumen; a distal anchor; and a tubular lining spanning an axial gap spatially separating the proximal tubular stent from the distal anchor, the tubular lining configured to exert a second radial force on the interior of the lumen along an axial portion of the lumen corresponding to the axial gap, the second radial force being in a range between (a) substantially zero and (b) less than the first radial force, the tubular lining substantially impermeable to an alimentary tract content.

The distal anchor may include a distal tubular stent having opposed proximal and distal end portions and being expandable from a collapsed state to an expanded state to exert a third radial force against the interior of the lumen, the third radial force being greater than the second radial force.

The proximal tubular stent may be tapered, e.g., frustoconical, in shape and have a proximal diameter larger than a distal diameter.

The distal tubular stent may have a cylindrical shape with a proximal diameter being substantially the same as a distal diameter.

The device second radial force may be substantially zero.

The at least one of the first and third radial forces may be 2 N (Newtons) or less when the respective proximal or distal tubular stent is compressed to a 25% reduction from a respective resting diameter.

The tubular lining may be configured to traverse a colonic anastomosis with the proximal and distal tubular stents being positioned on respective opposed sides of the colonic anastomosis.

The device may further include a cord extending distally beyond the distal tubular stent and being configured to be exteriorized through a rectum of the patient for adhesion to a buttock of the patient.

The tubular lining may be configured to cover an entire outer surface of each of the proximal and distal tubular stents.

A length of the proximal tubular stent may be shorter than a length of the distal tubular stent.

The distal anchor may include a distal ring.

The distal ring may be flexible.

The second radial force may be substantially zero.

The first radial force may be a differential radial force, wherein, by axial length, a proximal 25% of the proximal tubular stent exerts a higher radial force than a distal 75% of the proximal tubular stent.

The proximal tubular stent may be tapered, e.g., frustoconical, in shape with a proximal diameter larger than a distal diameter.

The ring may be configured to be disposed exterior to an anus of the patient when the device is implanted and may include an adjustment mechanism adapted to adjust an axial length of the tubular lining between the distal ring and the proximal tubular stent and an axial length of the gap.

The tubular lining may be adapted to traverse an anal canal of the patient.

The tubular lining may cover an entire outer surface of the proximal tubular stent.

The distal ring may be configured to be disposed on an exterior a body of the patient and the stent may be configured to be disposed in the lumen of a rectum of the patient when the device is implanted.

The proximal stent may be configured to be delivered in a collapsed state through a guidewire under endoscopic visualization.

The proximal tubular stent may be configured, when compressed to a 25% reduction in diameter from a resting diameter, to exert a radial force between 2 N and 3 N at a proximal portion of the proximal tubular stent and a radial force of less than 2 N at a distal portion of the proximal tubular stent.

In accordance with example embodiments of the present invention, a method of using the intraluminal protective device includes: placing the intraluminal protective device in an implanted position in the patient such that the tubular lining forms a protective barrier covering an anastomosis of the lumen, the device exerting a radial force at a location proximal to the anastomosis that is greater than a radial force exerted at the protective barrier; anchoring (e.g., temporarily) the intraluminal protective device in the implanted position at a location proximal to the anastomosis by radially expanding the protective device into an expanded state such that the device exerts a radial force on the interior of the lumen at a location proximal to the anastomosis that is greater than a radial force exerted on the interior of the lumen at the protective barrier; and anchoring (e.g., temporarily) the intraluminal protective device in the implanted position at a location distal to the anastomosis, wherein the protective barrier is impermeable to an alimentary tract content and configured to prevent the alimentary tract content from contacting the anastomosis when the protective device is anchored (e.g., temporarily) in at the locations proximal and distal to the anastomosis.

In accordance with example embodiments of the present invention, a method includes: placing an intraluminal protective device in an implanted position in a lumen of a patient such that a protective barrier of the protective device covers an anastomosis; anchoring (e.g., temporarily) the intraluminal protective device in the implanted position at a location proximal to the anastomosis by radially expanding the protective device into an expanded state such that the device exerts a radial force on an interior of the lumen at a location proximal to the anastomosis that is greater than a radial force exerted on the interior of the lumen at the protective barrier; and anchoring (e.g., temporarily) the intraluminal protective device in the implanted position at a location distal to the anastomosis, wherein the protective barrier is impermeable to an alimentary tract content and configured to prevent the alimentary tract content from contacting the anastomosis when the protective device is anchored in at the locations proximal and distal to the anastomosis.

The placing may include introducing the intraluminal protective device into the patient transanally.

The intraluminal protective device may be anchored (e.g., temporarily) by a first stent proximal to the protective barrier and a second stent distal to the protective barrier.

The anchoring may be performed by expanding each of the first and second stents from a respective contracted state to a respective expanded state.

The intraluminal protective device may be anchored by a stent proximal to the protective barrier and a ring distal to the protective barrier.

The intraluminal device may include a cord extending through an anus of the patient, the method further comprising adhering the cord to a buttock of the patient.

The method may further include removing the temporary intraluminal device from the patient by pulling the cord after separating the cord from the buttock of the patient.

In accordance with example embodiments of the present invention, a device for performing the method includes: a proximal tubular stent having opposed proximal and distal end portions and being expandable from a collapsed state to an expanded state to exert a first radial force against the interior of the lumen; a distal anchor; and a tubular lining spanning an axial gap separating the proximal tubular stent and the distal anchor, the tubular lining being configured to exert a second radial force on the interior of the lumen at a location along an axial portion of the lumen corresponding to the axial gap, the second radial force being in a range between (a) substantially zero and (b) less than the first radial force exerted by the proximal tubular stent, the tubular lining substantially impermeable to an alimentary tract content.

The subject invention is directed to new and useful temporary, intraluminal GI protective devices that are placed prophylactically at the time of surgery to protect a freshly constructed anastomosis, staple-line, or the like. The invention also provides a number of device choices depending on the location of use, for example one device for esophagus/gastric surgery, one device for pancreatic surgery, and another device for colon/rectum resection.

The invention includes an intraluminal protective device. The protective device includes a tubular stent having a proximal and distal end portions. The tubular stent is adapted and configured for movement from a first collapsed position to a second expanded position within the lumen of a patient. The protective device also includes a tubular lining operatively associated with substantially the entire outer perimeter of the tubular stent. The tubular lining is adapted and configured to cover and protect an anastomosis, staple-line or the like.

In certain embodiments, the diameter of the proximal end portion of the tubular stent is larger than the diameter of the remainder of the tubular stent. The larger diameter portion of the stent is adapted and configured to prevent migration of the stent after placement within a lumen of a patient. It is further contemplated that at least one ring can be operatively associated with the distal end portion of the lining.

In certain embodiments, a second tubular stent having a proximal and distal end portion is provided. The second stent is adapted and configured for movement from a first collapsed position to a second expanded position within a lumen of a patient. A tubular lining is operatively associated with the distal end portion of a first stent and the proximal end portion of the second tubular stent. The tubular lining is adapted and configured to cover and protect an anastomosis. It is contemplated that the tubular lining substantially covers the outside perimeter of the first and second stents.

To alleviate the undesirable effects of a GI leak after gastric bypass, sleeve gastrectomy, esophagectomy, gastrectomy, or pancreaticoduodenectomy, the current invention when used prophylactically at the time of surgery, will protect the anastomosis and staple-line and therefore reduce the leak rate or minimizes the severity of a leak. A further advantage is to alleviate the undesirable effects of a prophylactic ileostomy performed during colorectal surgery and the need for take down of the ileostomy. The current colon/rectal protective invention, when used prophylactically at the time of surgery, will protect the anastomosis and therefore, a prophylactic ileostomy can be avoided.

One exemplary embodiment of the current invention is a temporary colon/rectal device that can be placed prophylactically at the time of surgical resection to provide a barrier between the newly constructed rectal anastomosis and the fecal stream. In addition, the device acts as a conduit to divert the fecal stream through the anus and provide a mechanical scaffold to promote healing of the anastomosis.

In certain exemplary embodiments, a rectal device is presented which relates to a temporary, intraluminal protective rectal device that is placed prophylactically at the time of surgery to protect a freshly constructed anastomosis. As such, the present invention overcomes the shortcomings of, and provides advantages over the well known temporary, prophylactic ileostomy procedure. For instance, the present device protects the anastomosis from both increased intraluminal pressure and completely diverts the fecal stream whereas a diverting ileostomy does not completely prevent fecal matter and intraluminal pressure from contacting the anastomosis which does not truly protect the anastomosis.

An exemplary rectal protective embodiment includes or consists of a colon/rectum protector with an impermeable lining supported by an expandable stent like scaffold configured to keep the device open and an anal protector with a dual ring system separated by an impermeable lining, such as plastic, PTFE or silicon. The proximal ring is configured to be placed within the rectum and the distal ring is configured to be placed outside the patient's buttock on the anal verge. Both parts of the device are attached continuously by an impermeable lining, such as plastic, silicone or PTFE. The proximal diameter of the colon/rectum portion of the device can range between 35-45 mm and the body of the device can range from between about 30-35 mm. There is a loop within the anal protective portion of the device to transanal removal of the device.

In certain embodiments, the subject invention is directed to a temporary intraluminal rectal device including a protective barrier that is placed transanally to protect a freshly constructed rectal anastomosis. The method includes endoscopically placing a temporary intraluminal rectal device including or consisting of a protective barrier that is placed transanally, specifically to protect a freshly constructed rectal anastomosis.

The rectal device can be an endoscopic anastomotic protective device including an elongate conduit that conforms to the shape of the colon, rectum, and anus, is placed within the colon/rectum to divert the fecal stream, and has a lining that is impermeable to water and fecal matter. The rectal device may include or consist of two components, an anal protective barrier attached to a colon/rectum protective barrier.

The rectal device anal protective barrier can include an impermeable lining (plastic or silicone) separated by two flexible plastic rings. It is also contemplated that the rectal device may include or consist of a colon/rectum protective barrier including or consisting of a protective barrier that is maintained open with a self-expandable stent framework, otherwise known as a stent. It is contemplated that the rectal device can be positioned, as measured from the proximal end portion of the colon/rectum protective barrier, in the colon at 18-20 cm proximal to the anal canal. It is further contemplated that the rectal device can be positioned such that the distal end portion of the colon/rectum protective barrier can be placed within the rectum at 3-5 cm proximal to the anal canal. It is further contemplated that the rectal device can be positioned such that the distal end of the anal protective barrier is positioned exterior to the anus at 3-5 cm distal from the anal canal.

It is also contemplated that the rectal device can include an atraumatic feature on the proximal and distal end of the anal protective barrier. The atraumatic feature can be a plastic, flexible ring on the proximal and distal end of the anal protective barrier. It is further contemplated that the atraumatic feature of the colon/rectum protective barrier can be a stent framework.

In certain embodiments, the plastic, flexible ring on the proximal aspect of the anal protective barrier can have plastic loops attached on the inner surface for easy transanal removal. In certain embodiments, a water impermeable coating or lining can be around the elongate body of the device.

The invention also includes a method for deploying the rectal or colonic protective device to be positioned within the colon or rectum, the method comprising the steps of loading the colon/rectum portion of the device onto a catheter delivery system and the anal protective barrier portion of the system being attached to the catheter delivery system. The method can also include the step of endoscopy being performed with placement of a stiff guide wire up toward the proximal colon.

The step of endoscopy being performed can include the loaded catheter delivery system being positioned within the proximal colon/rectum using the guide wire, approximately 18-20 cm proximal to the anal canal. It is also contemplated that the colon/rectum portion of the device can be deployed under direct endoscopic visualization by pulling back on the sheath covering the catheter delivery system.

The method for deploying the rectal protective device can further include the steps of manually inserting the proximal ring through the anus to be positioned immediately proximal to the anal canal once the colon/rectum portion of the device is deployed. The method can further include the step of once the colon/rectum portion of the device is deployed, the distal ring of the anal protective portion of the device can be manually tightened by rolling outward until the two rings (proximal and distal rings) are securely positioned across the anal canal. It can be further envisioned that the anal protective barrier portion of the device can be retained in place with the use of the two proximal and distal transanal rings that is positioned 3-5 cm from the anal verge.

In certain embodiments, the method of removing the rectal protective device can further include the step of removing the implanted device by inserting a finger transanally to hook onto the plastic loops that are attached to the inner surface of the proximal anal ring. The method can further include pulling on the loop which will result in removal of the proximal ring. The method can further include that further pulling of the entire device will result in transanal removal of the colon/rectal protective barrier.

Unlike the use of prophylactic ileostomy which requires surgical take down of the ileostomy under general anesthesia, removal of the current device can be performed by extraction through the anus and can be accomplish in the office setting without the use of sedation. Unlike the timeline for take down of a diverting ileostomy which takes place approximately between about 6-8 weeks, the current device will typically only be required to be in place for approximately 2-3 weeks.

In certain embodiments, an esophageal/gastric device is provided which relates to a temporary, intraluminal protective device that is placed prophylactically at the time of surgery to protect a freshly constructed anastomosis or gastric staple-line. As such, the present invention overcomes the shortcomings of an anastomotic leak complication after GI surgery. In order to deploy the device, the entire esophageal/gastric device is package into a small delivery system. Upper endoscopy is performed after completion of the esophagogastrectomy, gastric bypass or sleeve gastrectomy. A guide wire is positioned into the small bowel in case of gastric bypass or into the gastric antrum in case of sleeve gastrectomy. The catheter delivery system is placed over the guidewire and deployed accordingly. The distal stent is deployed first below the gastroesophageal junction or anastomosis and the proximal stent is then deployed above the gastroesophageal junction or anastomosis. All deployment is performed under direct visualization with the endoscope sitting adjacent to the catheter delivery system.

An exemplary esophageal/gastric protective embodiment includes or consists of a short stent positioned within the esophagus and a longer stent positioned within the stomach (in sleeve gastrectomy and esophagectomy) or positioned through the anastomosis (in gastric bypass). Both parts of the device are attached continuously by an impermeable lining, such as plastic, PTFE or silicone. The design of a proximal and distal stent bridged by an impermeable membrane is configured to minimize or prevent proximal and distal migration of the stent. The proximal diameter of the esophageal portion of the device can range from between about 28-30 mm and the body of the distal stent device can range from between about 23-25 mm.

In certain embodiments, a temporary intraluminal esophageal/gastric device including a protective barrier is placed transorally to protect a freshly constructed esophageal/gastric staple-line or anastomosis. In certain embodiments, the esophageal/gastric device can be an endoscopic anastomotic or staple-line protective device including an elongated conduit that conforms to the shape of the esophagus and stomach. It is contemplated that the esophageal/gastric device can be placed within the esophagus and stomach to divert the GI content. It is also contemplated that the esophageal/gastric device includes a lining that is impermeable to water and GI content.

In certain embodiments, the esophageal/gastric device can be constructed of two components including an esophageal protective portion and a gastric protective portion that are connected by an impermeable barrier.

It is contemplated that the esophageal protective portion of the esophageal/gastric device can be configured to be positioned within the esophagus and can measure between about 4-5 cm in length. It is further contemplated that the gastric protective portion of the device can be configured to be positioned within the stomach below the gastroesophageal junction or anastomosis and can measure between about 8-10 cm.

In certain embodiments, the proximal diameter of the esophagogastric portion of the device can measure between about 28-30 cm and the diameter of the body of the device can measure between about 23-25 cm. It is contemplated that the body of the esophageal/gastric protective device can include a water impermeable coating or lining around the elongated body.

The invention also includes a method of endoscopically placing a temporary intraluminal esophageal/gastric device. The method includes a protective barrier that is placed transorally, specifically to protect a freshly constructed esophageal/gastric anastomosis.

It is also contemplated that a method can be directed to removing an intraluminal esophageal/gastric device. The method includes the step of endoscopically grasping a suture located at the top aspect of the stent. The method also includes pulling on the suture resulting in transoral removal of both the esophageal and gastric portions of the esophageal/gastric device.

In certain embodiments, a colonic protective device is configured similar to the esophagus/gastric device with two stents deployed, one stent above and one stent below the colon anastomosis and connected by a continuous impermeable barrier. The colonic protective device is placed to protect the anastomosis. The colonic protective device can be about 38-45 cm in proximal diameter and about 18-20 cm in length. A cord can be attached to the distal end portion of the device to allow removal of the colonic protective device after approximately about 2-3 weeks once the anastomosis has sufficiently healed. A ring can be attached to the distal end of the cord exterior to the anal canal to further facilitate removal of the colonic protective device by enabling a doctor to provide traction on the colonic protective device. To insert the device into a patient, the device is packaged into a small catheter-based delivery system. Colonoscopy is performed and a guide wire is passed into the proximal colon. The catheter delivery system is passed over the guide wire and positioned within the proximal colon. This is performed under direct endoscopic visualization with a colonoscope positioned adjacent to the catheter delivery system. The first stent is deployed above the anastomosis and the second stent is deployed below the anastomosis. Once the device is deployed, the endoscope is removed. A cord attached to the distal end of the device is taped to the patient's buttock to facilitate removal of the device.

In certain embodiments, a pancreatic protective device is provided which relates to a temporary, intraluminal protective device that is placed prophylactically at the time of surgery to protect a freshly constructed anastomosis. As such, the present invention overcomes the shortcomings of an anastomotic leak complication after GI surgery. In order to deploy the device, the entire pancreatic device is package into a small delivery system. Under direct visualization, a guide wire is positioned into the pancreatic duct. The catheter delivery system is placed over the guidewire and deployed accordingly.

These and other features of the systems and methods of the subject invention will become more readily apparent to those skilled in the art from the following detailed description of the preferred embodiments taken in conjunction with the drawings.

BRIEF DESCRIPTION OF THE DRAWINGS

So that those skilled in the art to which the subject invention appertains will readily understand how to make and use the devices and methods of the subject invention without undue experimentation, preferred embodiments thereof will be described in detail herein below with reference to certain figures, wherein:

FIGS. 11 and 12 are partial views of protective devices having frustoconical stents.

FIGS. 13 to 15 show protective devices having membranes of differing axial extensions.

DETAILED DESCRIPTION

Figure 1:
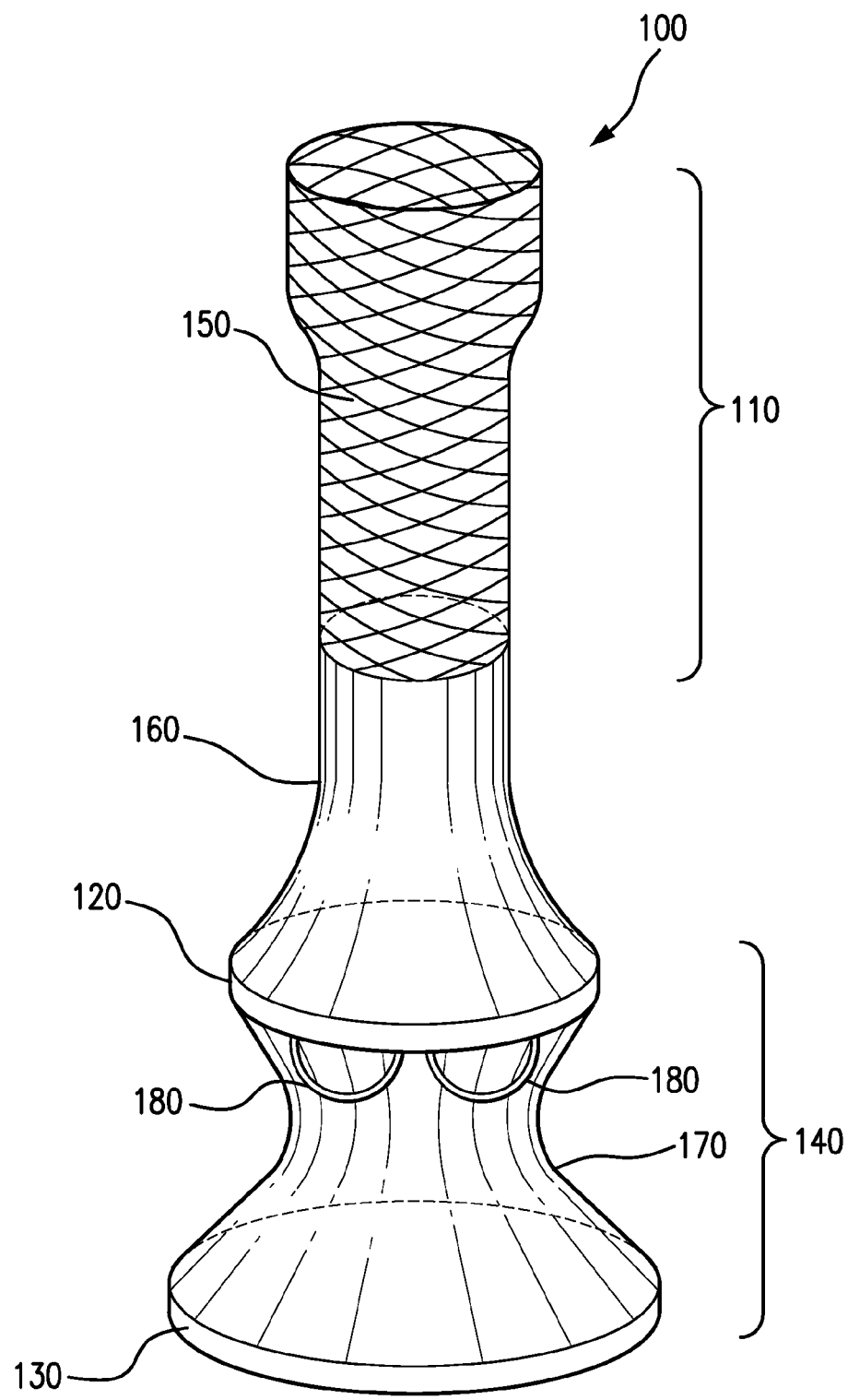
FIG. 1 is a perspective view of an exemplary embodiment of a device constructed in accordance with the present invention, showing a colon/rectum implant device that is divided into a colon/rectum protective portion and anal protective portion.

Reference will now be made to the drawings wherein like reference numerals identify similar structural features or aspects of the subject invention. For purposes of explanation and illustration, and not limitation, a partial view of an exemplary embodiment of a rectal device in accordance with the invention is shown in FIG. 1 and is designated generally by reference character 100. Other embodiments of the device in accordance with the invention, or aspects thereof, are provided in FIGS. 2-10, as will be described. The system of the invention can be used to overcome shortcomings GI leaks or the need of the prophylactic ileostomy described above.

For the rectal application, the present device overcomes shortcomings of the ileostomy described above by providing an implant device that is secured to the colon/rectum and traversing the anal canal that is used for protection of a freshly constructed rectal anastomosis. The protection may promote healing of the anastomosis by creating an axially secured barrier to alimentary tract content while applying a low amount of pressure, if any, on the anastomosis. The present invention provides a colon/rectum protective barrier and an anal canal protective barrier. The present invention also provides a mechanism for removal of the device through the anus by pulling on the loops attached to the distal ring of the anal protective portion of the device. These, and other, aspects of the present invention are provided in further detail below.

While the prophylactic implant device in the exemplary embodiments presented herein may be used within the esophagus, stomach, colon/rectum and anus, it is understood that these are exemplary embodiments presented to demonstrate aspects of the present invention. The description provided herein may refer to the deployment of an implant device in particular to the esophagus, stomach, colon and rectum, but it is also understood that aspects of the present invention may be employed within other part of the gastrointestinal tract such as the small intestine and biliary tract.

Accordingly, a temporary protective rectal device 100 according to an embodiment of the present invention is illustrated in the exemplary embodiment of FIG. 1. The temporary protective rectal device 100, is generally deployed within the colon or rectum in order to protect and promote the healing of a freshly constructed anastomosis and hence to prevent leaks, anastomotic dehiscence, and intra-abdominal abscess. The top aspect of the device shown in FIG. 1 depicts the colon/rectum protective portion 110 of the device. The device includes or consists of a water impermeable membrane, such as plastic, silicone or PTFE, that is supported by a self expanding metal framework, also referred to as a stent 150. The top and bottom portion of the device is attached by a continuous impermeable membrane 160, such as plastic, silicone or PTFE.

The lower aspect of the device shown in FIG. 1 depicts the anal protective portion 140 of the device which includes or consists of a proximal flexible ring 120 and a distal flexible ring 130, constructed out of a suitably flexible material, such as plastic, silicone or PTFE, that are attached to each other by an impermeable membrane 170, such as plastic, PTFE or silicone.

The proximal aspect of the device measures from between about 35-45 cm to accommodate the diameter of the colon or rectum. The proximal aspect is kept open by a stent 150. An impermeable lining covers the outer circumference of the stent 150. As further illustrated in FIG. 1, the proximal ring 120 of the anal protective portion 140 of the device measures from between about 35-45 cm in diameter and the distal ring 130 of the anal protective portion 140 measures from between about 45-55 cm in diameter. Interior loops 180 may be connected to the proximal ring 120 in order to facilitate removal of the temporary protective rectal device 100. The method of removal of the device 100 is described and shown below in FIG. 4.

Figure 2:
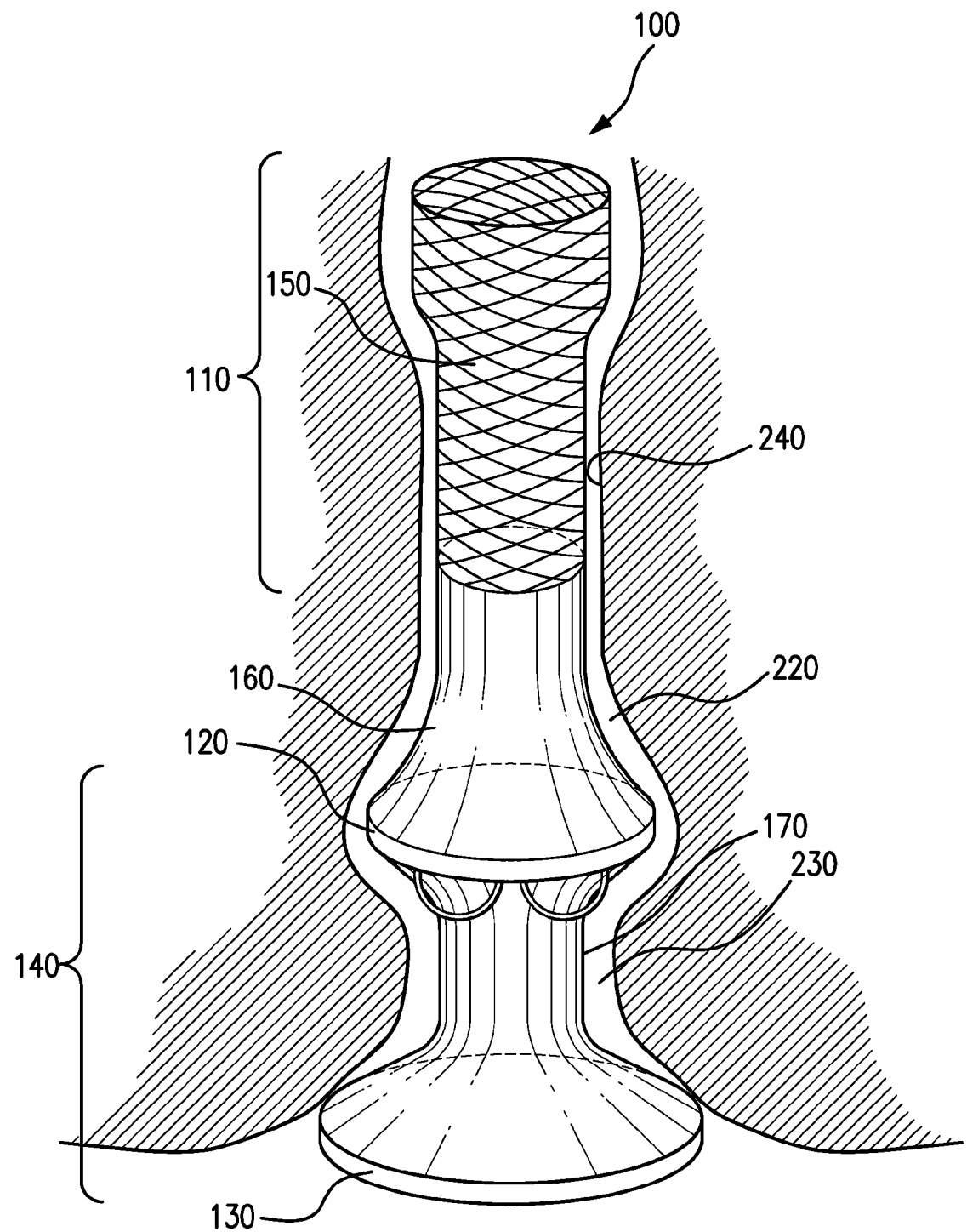
FIG. 2 is a perspective view of the device of FIG. 1 implanted within the colon or rectum and the position of the anal protective portion of the device traversing the anal canal.

Referring now to FIG. 2, the colon/rectum protective portion 110 of the device is positioned within the colon/rectum and the anal protective portion 140 of the device is positioned within the anal canal 230 with the proximal and distal rings 120, 130 traversing the anal canal 230. The colon/rectum protective portion 110 is held in place by the force of the expansion of the stent 150 against the colon or rectum wall 240. In this regard, the stent 150 exerts a radial force onto the interior of the colon or rectum wall 240 in order to provide a distal anchor or support to axially secure the device 100 at the location of the stent 150 proximal to an anastomosis location 220. Further, the distal ring 130, which has a diameter sufficiently large to prevent, or at least resist, entry of the distal ring 130 into the patient's anus, provides a distal anchor or support to axially secure the device 100 at the location of the ring 130, which is distal to the anastomosis location 220.

The impermeable barrier 170 connecting the proximal and distal rings 120, 130 is configured to be able to be axially compressed by the anal canal 230 to allow normal functioning of the anal canal 230. The proximal aspect of the colon/rectum protective portion 110 of the device is positioned at approximately from about 18-20 cm as measured from the top (distal end) of the stent proximal to the anal canal 230. The anastomosis location 220 is protected by an impermeable membrane 160, which forms a tubular lining. The length of the impermeable membrane 160 portion between the colon/rectum protective portion 110 and the proximal ring 120 can be about 4-6 cm. The impermeable membrane 160 also can cover the outer periphery of the stent 150.

The impermeable membrane 160 promotes healing of the anastomosis by creating an axially secured barrier to alimentary tract content while applying a low amount of force and pressure, if any, on the anastomosis. In this regard, the ability to block alimentary tract content, which impedes healing and may lead to infection or other complications, while applying little or no pressure provides an optimal healing environment for the anastomosis while allowing the alimentary tract content to pass axially through the anastomosis location 220. Thus, the device 100 allows for healing of the anastomosis without interrupting or rerouting the alimentary tract.

The low or substantially non-existent radial force applied by the membrane 160 onto the anastomosis is achieved by the configuration of the device 100 to apply different levels of force and pressure at different axial locations. In particular, the stent 150 applies a relatively high level of radial force, e.g., a force in a range from 2 N to 3N, in order to axially secure the device 100 proximal to the anastomosis location 220. Since the stent 150 axially terminates at a location proximal to the anastomosis, this anchoring force is not exerted onto the anastomosis via the membrane 160. Similarly the anchoring mechanism provided by the ring 130 and/or ring 120 axially secures the device 100 at a location distal to the anastomosis location 220. Thus, the membrane 160 is axially supported in the location of the anastomosis.

Further, the radial forces exerted by the stent 150 allow the proximal end of the membrane to form a seal with the surrounding tissue to prevent the alimentary tract content from flowing into a space radially between the membrane 160 and the tissue of the patient's lumen. Similarly, the alimentary tract content is prevented from entering the distal end of the membrane 120 by a seal formed by rings 120 and/or 130 and or the continuation of membrane surface to the exterior of the patient.

Figure 3:
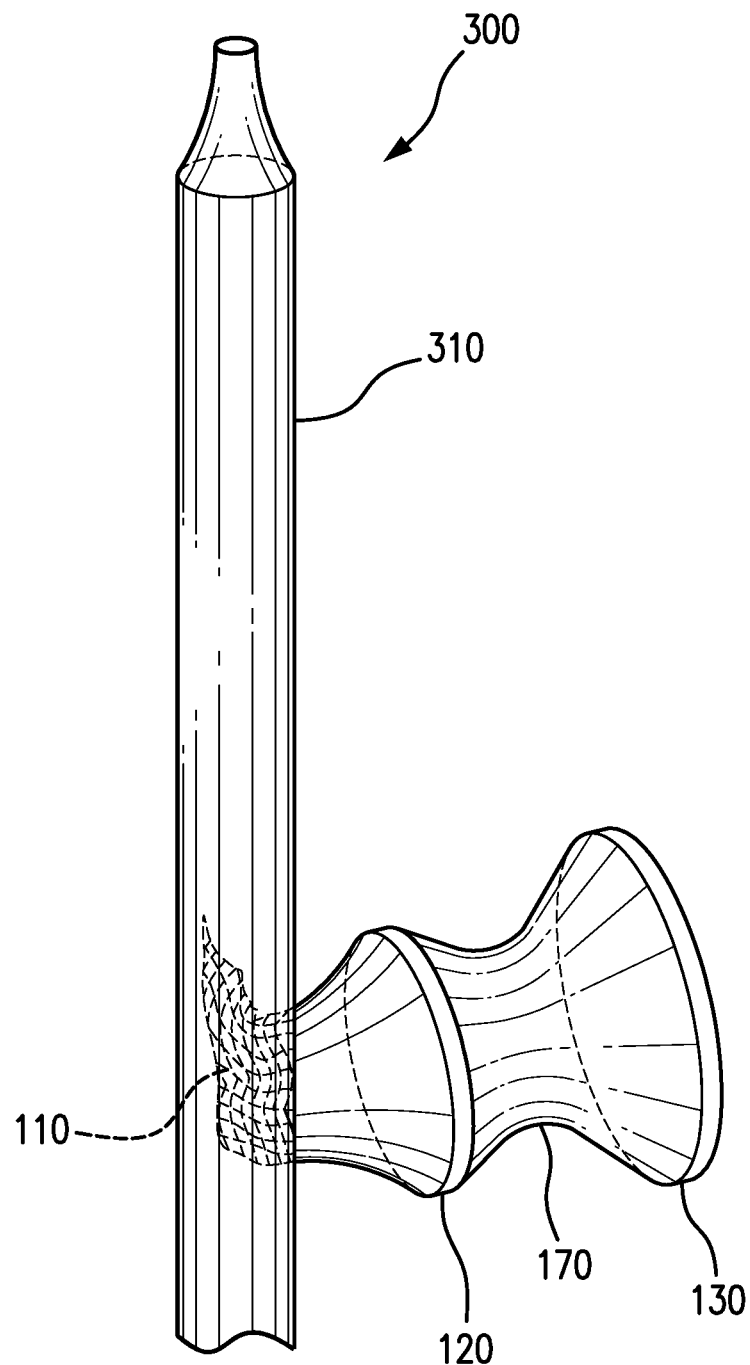
FIG. 3 is a perspective view of the device of FIG. 1 encased within a delivery catheter system with the anal protective portion of the device hanging off to the side of the system.

Device 100 can be packaged into a small catheter delivery system 300 as shown in FIG. 3. The colon/rectum protective portion 110 of the device is compressed within a sheath 310. Once the device is positioned in the desired implanted location within the colon or rectum, the sheath is removed to deploy the stent 150 from its collapsed state to the expanded state as shown in FIG. 2. Subsequently, the distal ring 120 of the anal protective portion 140 of the device is inserted transanally to be positioned within about 2-4 cm from the anal canal. The distal ring 130 may be folded outwardly to tighten the tension of the impermeable membrane 170 of the device within the anal canal 230 as desired.

Figure 4:
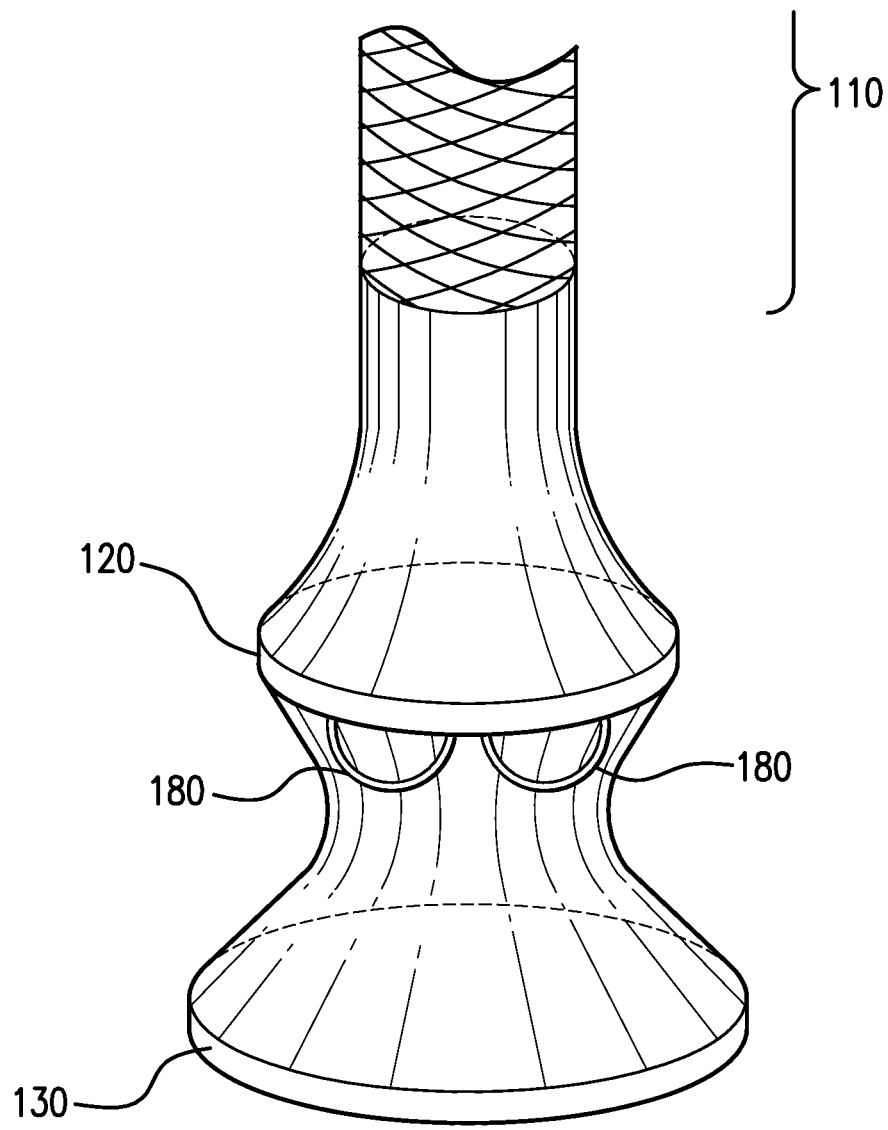
FIG. 4 is a perspective view of the anal protective portion of the device of FIG. 1, showing interior loops that are used for removal of the device through the anus.

Referring now to FIG. 4, the interior loops 180 are attached to the proximal ring 120. These loops can be used for removal of the proximal ring through the anus. The surgeon can insert a digit to find one of the loops 180 and hook the loop 180 to pull out the proximal ring 120 transanally. Upon removal of the proximal ring 120, the rest of the device 100 can be removed by placing traction on the impermeable lining that is continuously attached to the colon/rectum protective portion 110 of the device 100.

In another exemplary embodiment, an esophagus/gastric protective device is presented. The esophagus/gastric protective device overcomes shortcomings of leak complications after surgery, such as gastric bypass surgery, by providing an implant device that is secured to the esophagus and traverses the gastroesophageal junction with an impermeable membrane. A distal aspect of the device is deployed within the stomach pouch traversing the anastomosis or positioned within the stomach. The present invention provides an esophageal protective membrane that will be used to anchor the device within the esophagus, thereby preventing migration. There is a continuous impermeable membrane traversing the gastroesophageal junction that is connected to the distal aspect of the device which is deployed to be positioned within the gastric pouch or gastric sleeve. The esophagus/gastric protective device may also overcome shortcomings of leak complications after surgery, such as esophagectomy, by providing an implant device that is secured to the esophagus and traverses the anastomosis with an impermeable membrane that forms a tubular lining. A distal aspect of the device is deployed within the gastric conduit. The present invention provides an esophageal protective membrane that will be used to anchor the device within the esophagus, thereby preventing migration. There is a continuous impermeable membrane forming a tubular lining traversing the gastroesophageal anastomosis that is connected to the proximal aspect of the device which is deployed to be positioned within the esophagus.

Figure 5:
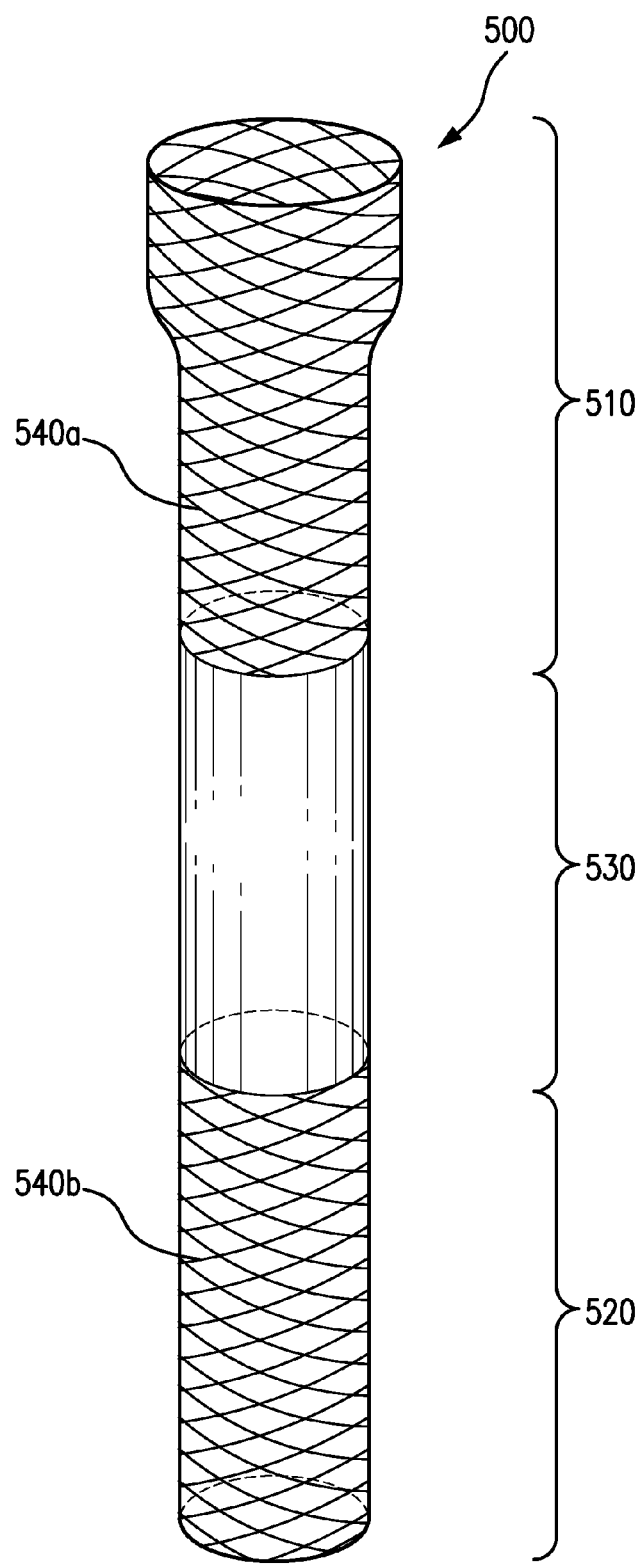
FIG. 5 is a perspective view of an exemplary embodiment of a device constructed in accordance with the present invention, showing an esophageal/gastric implant device that is divided into the esophageal protective portion and gastric protective portion.
Figure 6:
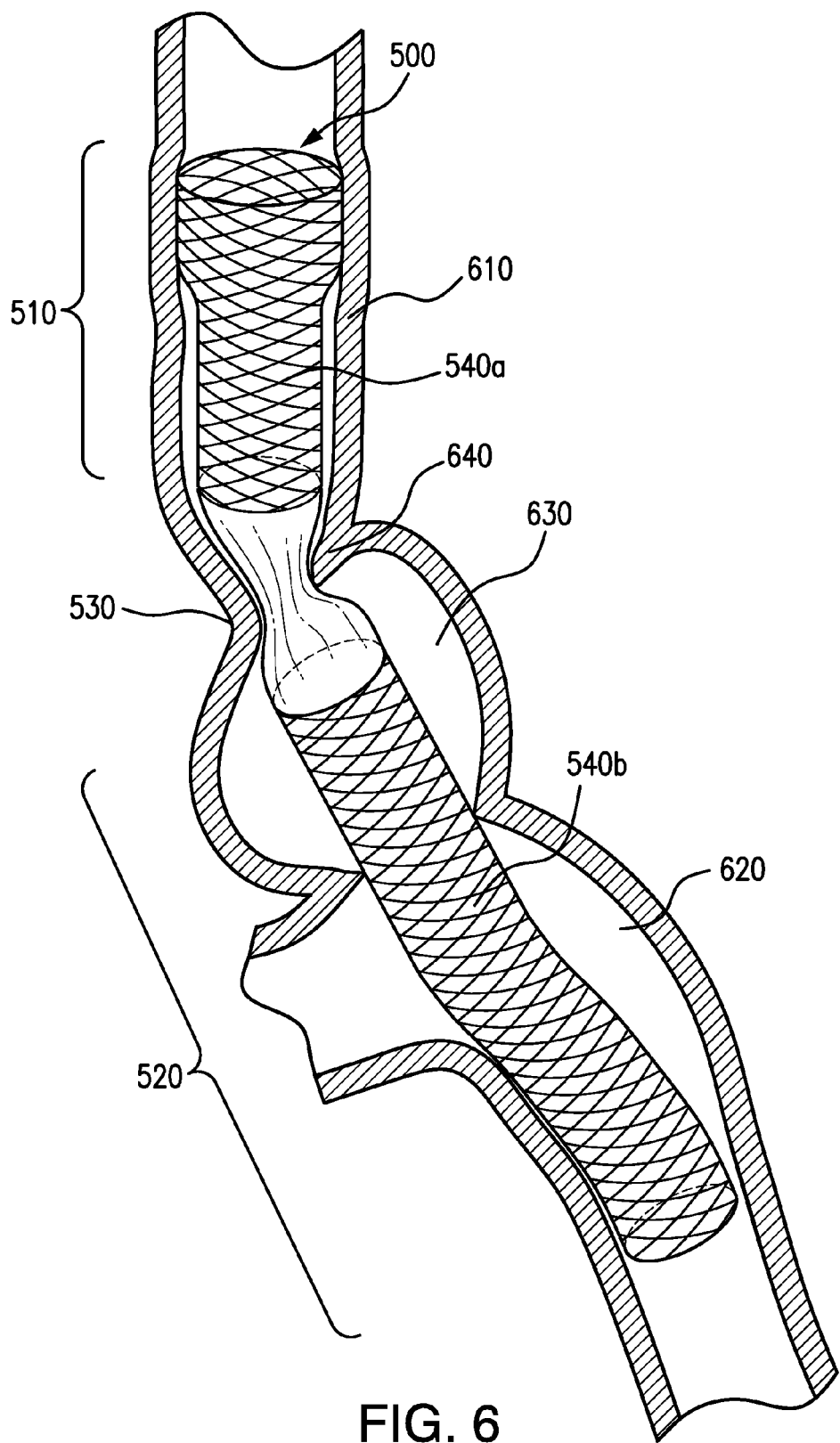
FIG. 6 is a perspective view of an exemplary esophageal/gastric protective device constructed in accordance with the present invention, showing the device implanted within a Roux-en-Y gastric bypass case whereby the esophageal protective portion is positioned within the esophagus and the gastric protective portion of the device is positioned within the gastric pouch, traversing the anastomosis.

Accordingly, a temporary protective esophageal/gastric device 500 according to an exemplary embodiment of the present invention is illustrated in FIG. 5. The esophageal/gastric protective device 500 is generally deployed within the esophagus and stomach, as shown in FIG. 6, in order to protect a freshly constructed anastomosis or gastric stapleline and thereby further prevent leaks, anastomotic dehiscence, and intra-abdominal abscess. The top aspect of the device 500 shown in FIG. 5 depicts the esophageal protective portion 510 of the device that is connected to the gastric protective portion 520 of the device 500. The two portions 510, 520 are connected by a water impermeable membrane 530.

The esophageal protective portion 510 of the device 500 has a proximal opening that measures between about 28-30 cm to accommodate the diameter of the esophagus and is kept open by a self expanding metal framework, or stent 540a. The diameter of the body of the stent 540a measures between about 23-25 cm. An impermeable membrane may be provided to cover the entire outside of the stent 540a of the esophageal protective portion 510. As further illustrated in FIG. 5, the gastric protective portion 520 of the stent 540b has a diameter that measures between about 23-25 cm. The esophageal 510 and gastric 520 protective portions are connected by one continuous impermeable membrane 530. The impermeable membrane 530 section between the esophageal 510 and gastric 520 protective portions can measure about 4-5 cm in length. A suture may be attached to the proximal end of the esophageal protective portion 510 stent 540 to facilitate endoscopic transoral removal of the device 500. The diameter of the proximal end portion of the stent 540a may be larger than the diameter of the remainder of the stent 540a where the larger diameter portion of the stent is adapted and configured to prevent migration of the stent 540a after placement within the esophagus of a patient.

Referring now to FIG. 6, the esophageal/gastric protective device 500 is shown deployed within the anatomic configuration of a Roux-en-Y gastric bypass. The esophageal protective portion 510 of the device 500 is positioned within the esophagus 610 and the gastric protective portion 520 of the device 500 is positioned within the stomach pouch 630 and traversing the gastrojejunal anastomosis 620. The anastomosis is protected by the gastric protective portion 520 of the device 500. The flexible impermeable membrane 530 between the two stents 540a, 540b of the esophageal protective portion 510 and the gastric protective portion 520 is positioned at the gastroesophageal junction 640. The flexible impermeable membrane 530 may cover the all or less than the entirety of the outside of the device 500. The flexible impermeable membrane 530 may, for example, leave axial portions of one or both stents 540a, 540b radially exposed to the surrounding luminal tissue. This arrangement may be desirable, e.g., to provide additional gripping of the stents into the tissue due to, e.g., the frictional properties of the open-weave or lattice-like nature of the wire stents 540a, 540b.

Figure 7:
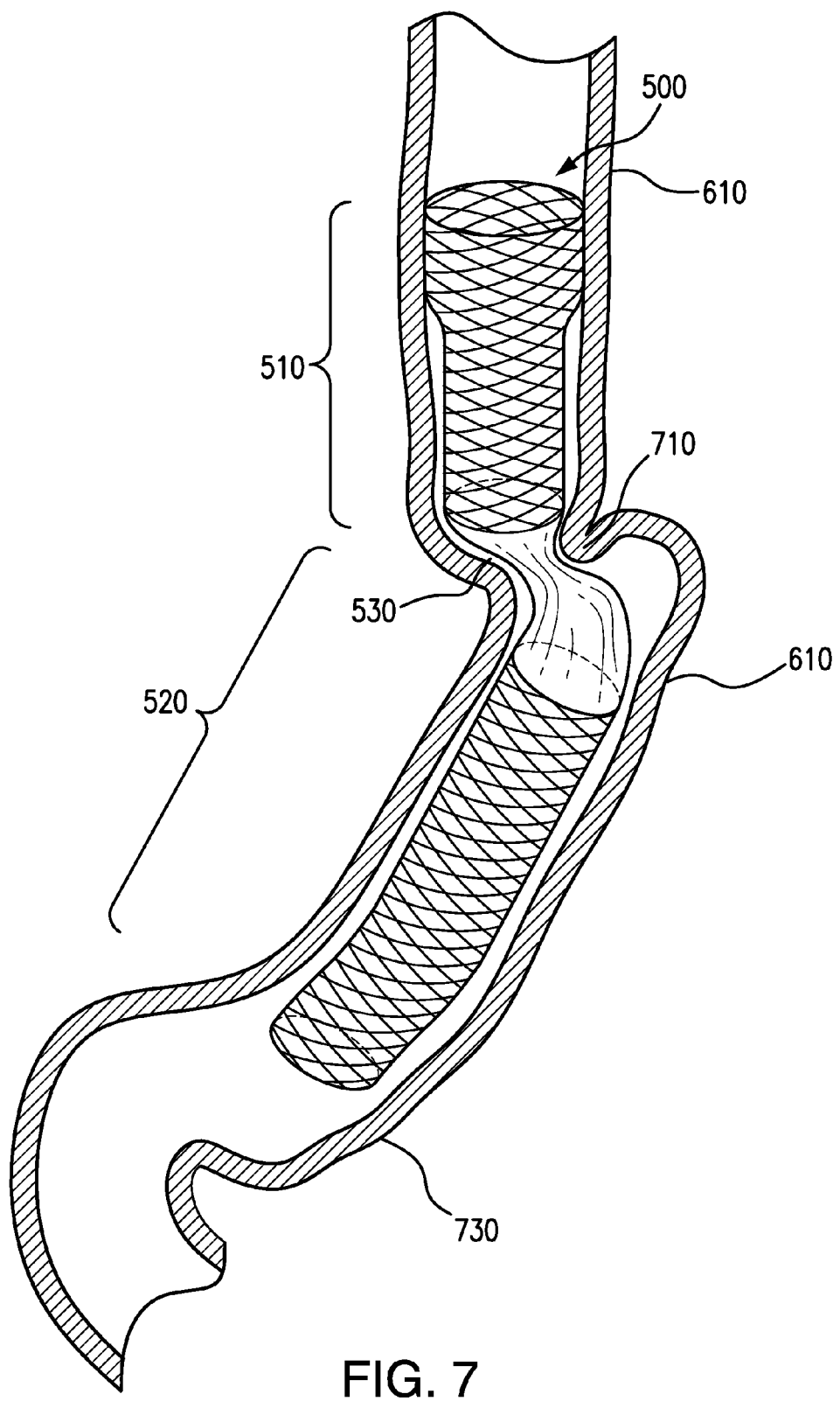
FIG. 7 is a perspective view of the esophageal/gastric device of FIG. 6, showing the device implanted within a sleeve gastrectomy case whereby the esophageal protective portion is positioned within the esophagus and the gastric protective portion of the device is positioned within the gastric sleeve with the distal aspect of the device located within the gastric antrum.

As illustrated in FIGS. 6 and 7, the axial length of the distal stent 540b is greater than the axial length of the proximal stent 540a.

As further illustrated in FIGS. 6 and 7, the proximal stent 540a is tapered, such that its proximal diameter is greater than its distal diameter. This arrangement may facilitate resistance of the proximal stent 540a to axially dislodging in the distal direction. This result may be achieved, e.g., by provision of a differential force exerted by the proximal stent 540a onto the surrounding tissue. For example, by axial length, the proximal 25% of the proximal tubular stent 540a may exert a higher radial force than the remaining distal 75% of the proximal tubular stent 540a.

With reference now to FIG. 7, the esophageal/gastric protective device 500 is shown deployed within the anatomic configuration of a sleeve gastrectomy. The esophageal protective portion 510 of the device is positioned within the esophagus 610 with the impermeable membrane 530 traversing the gastroesophageal junction 710 and the gastric protective portion 520 of the device 500 is positioned within the gastric sleeve 720 with the bottom of the gastric protective portion 520 positioned within the gastric antrum 730.

Figure 8:
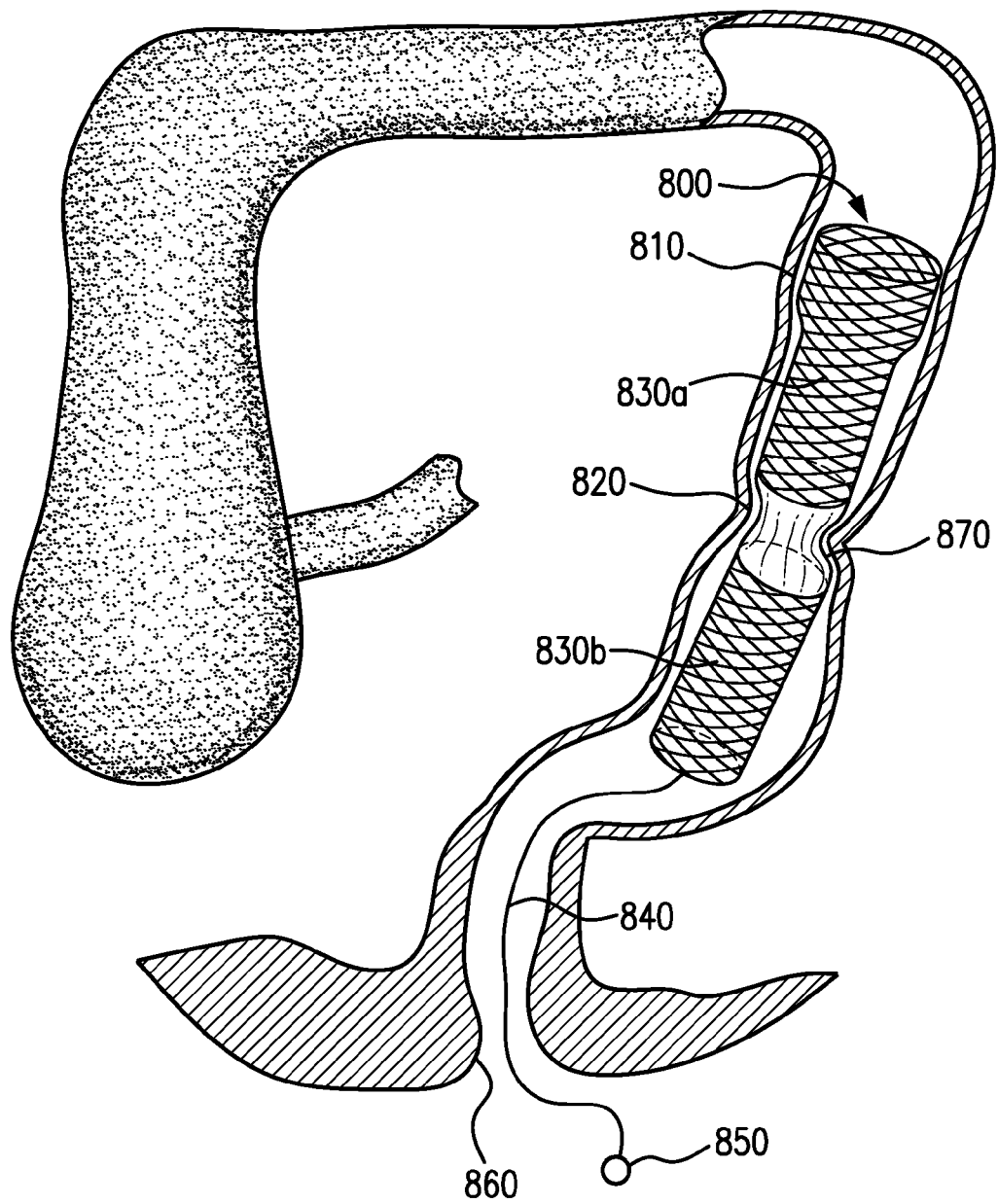
FIG. 8 is a perspective view of an exemplary embodiment of a colonic device constructed in accordance with the present invention, showing the device implanted within a left colectomy or sigmoidectomy case whereby the colonic protective device is positioned within the colon which has a cord attached to the distal aspect of the device for removal.

In another exemplary embodiment, FIG. 8 shows a colonic device 800 implanted within a left colectomy case whereby the colonic protective device 800 is positioned within the colon 810. In the illustrated embodiment, the colonic protective device 800 is configured as a two stents 830a, 830b connected by a continuous impermeable membrane 870. The colonic protective device 800 is placed to protect the anastomosis 820. The colonic protective device 800 may be, e.g., about 38-45 cm in diameter and about 18-20 cm in length. The proximal portion of the colonic device 800 may be, e.g., about 7-8 cm in length and the distal portion of the device 800 may be, e.g., about 5-6 cm in length. The impermeable membrane 870 traversing the colonic anastomosis 820 may be, e.g., about 4-5 cm in length.

A cord 840 is attached to the proximal end portion of the device 800 to allow removal of the colonic protective device 800, e.g., after approximately about 2 weeks once the anastomosis 820 has sufficiently healed. A ring 850 is attached to the proximal end of the cord 840 exterior to the anal canal 860 to further facilitate removal of the colonic protective device 800 by enabling a doctor to provide traction on the colonic protective device 800. A suture may be attached to the distal end of the colonic protective device 800, e.g., the distal end of the distal stent 830b in the illustrated example, to facilitate endoscopic removal of the device 800.

The impermeable membrane 870 promotes healing of the anastomosis 820 by creating an axially secured barrier to alimentary tract content while applying a low amount of force and pressure, if any, on the anastomosis 820. In this regard, as with other examples described herein, the ability to block alimentary tract content, which impedes healing and may lead to infection or other complications, while applying little or no pressure to the anastomosis 820 provides an optimal healing environment for the anastomosis 820 while allowing the alimentary tract content to pass axially through the axial location of the anastomosis 820. Thus, the device 800 allows for healing of the anastomosis 820 without interrupting or rerouting the alimentary tract.

The low or substantially non-existent radial force applied by the membrane 870 onto the anastomosis is achieved by the configuration of the device 800 to apply different levels of force and pressure at different axial locations. In particular, the proximal stent 830a applies a relatively high level of radial force, e.g., a force in a range from 2 N to 3N, in order to axially secure the device 800 at a location proximal to the anastomosis location 820. Since the proximal stent 830a axially terminates at a location proximal to the anastomosis 820, this anchoring force is not exerted onto the anastomosis 820 via the membrane 820. Similarly the anchoring mechanism provided by the distal stent 830b axially secures the device 800 at a location distal to the axial location of the anastomosis 820. Thus, the membrane 870 is axially supported in the location of the anastomosis 820. As with the proximal stent 830a, the distal stent 830b may apply a relatively high level of radial force, e.g., a force in a range from 2 N to 3N. Thus, the stents 830a and 830b apply radially forces that are substantially greater than any radial force applied by the membrane 870 at the location of the anastomosis 820.

The radial force exerted by the proximal stent 830a may be the same or different than the radial force exerted by the distal stent 830b.

The proximal stent 830a is tapered, such that its proximal diameter is greater than its distal diameter. This arrangement may facilitate resistance of the proximal stent 830a to axial dislodgement in the distal direction. This result may be achieved, e.g., by provision of a differential force exerted by the proximal stent 830a onto the surrounding tissue. For example, by axial length, the proximal 25% of the proximal tubular stent 830a may exert a higher radial force than the remaining distal 75% of the proximal tubular stent 830a.

Although the distal tubular stent 830b is cylindrical in shape, having a proximal diameter that is substantially the same as a distal diameter. It should be understood, however, that the distal stent 830 may have a tapered configuration with a proximal diameter larger than a distal diameter. Further, either or both of the distal and proximal stents 830a, 830b may be tapered, cylindrical, or any other suitable geometry. Further, the lengths of the proximal and distal stents 830a, 830b may be the same or differ. For example, the proximal stent 830a may be longer than the distal stent 830b, or vice-versa. However, it may be advantageous for the proximal stent 830a to be longer in order to apply greater anchoring force relative to the distal stent 830b. This is because, in the illustrated embodiment, the alimentary tract content flows in the distal direction, thus, the proximal stent may bear a greater amount of the anchoring load due to, e.g., frictional forces exerted onto the flexible membrane 870 and the corresponding tensional load.

Further, the radial forces exerted by the stents 830*a*, 830*b* allow the membrane 870 to form respective proximal and distal seals with the surrounding tissue to prevent the alimentary tract content from flowing distally or proximally into a space radially between the membrane 870 and the tissue of the patient's lumen. In this regard, the proximal and distal seals are formed by the relatively high pressures and forces applied locally by the stents 540*a*, 540*b* at respective locations proximal and distal to the anastomosis 820. Thus, a sealed barrier is formed over the anastomosis without applying substantial force and/or pressure to the anastomosis 820.

The stents 830*a* and/or 830*b*, or any other stents described herein, may exert a radial force of 2 N or less when the respective proximal or distal tubular stent 830*a*, 830*b* is compressed to a 25% reduction from a respective resting diameter.

Figure 9:
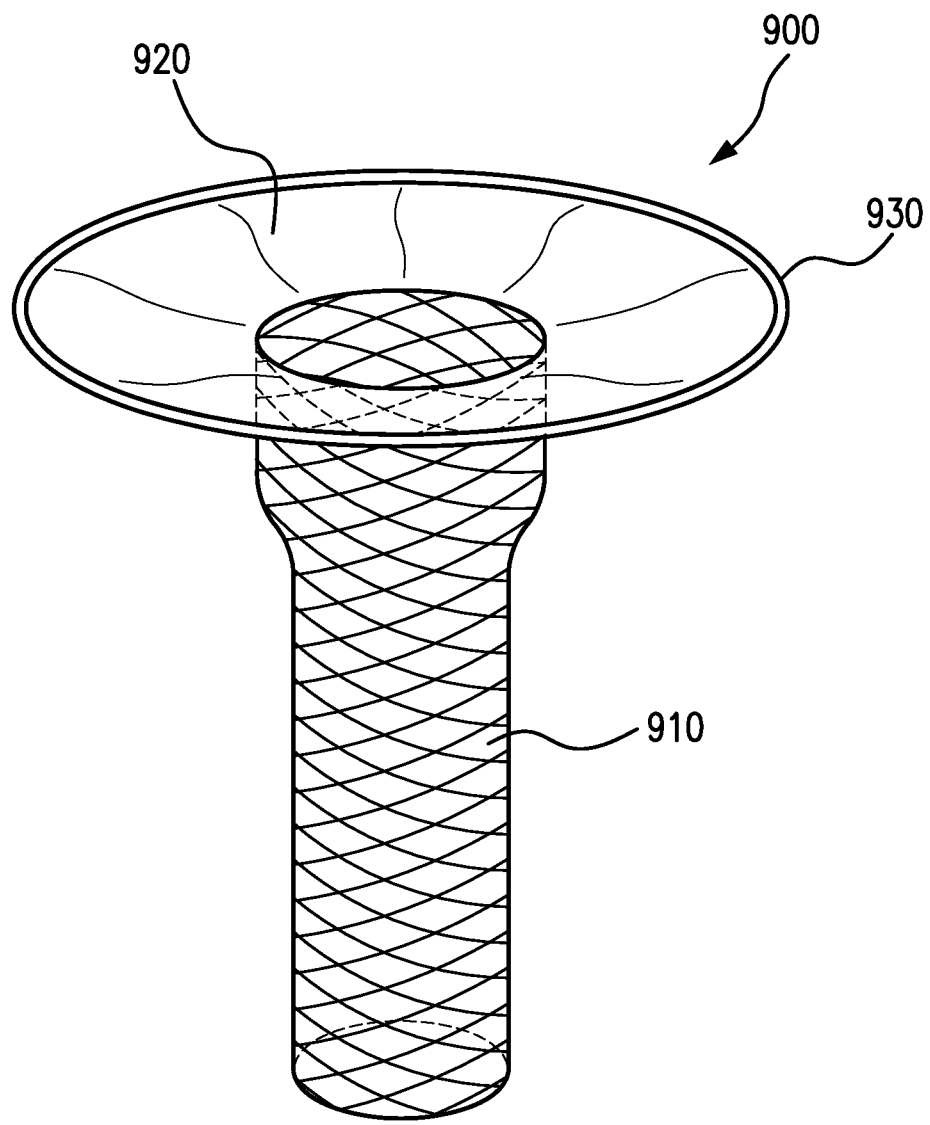
FIG. 9 is a perspective view of an exemplary embodiment of a pancreatic device constructed in accordance with the present invention, illustrating a pancreatic protective device that is divided into a pancreatic protective portion and a small bowel protective portion.

In another exemplary embodiment, FIG. 9 shows a pancreatic/biliary protective device 900. The pancreatic/biliary protective device 900 overcomes shortcomings of leak complications after surgery, such as, e.g., pancreaticoduodenectomy (Whipple) surgery, by providing an implant device that is implanted within the biliary duct or pancreatic duct and traverses the pancreatic small bowel anastomosis with an impermeable membrane 920. A stent 910 approximately 0.4-1.2 cm in diameter and 3-4 cm in length is connected to an outer ring 930 by the impermeable membrane 920.

Figure 10:
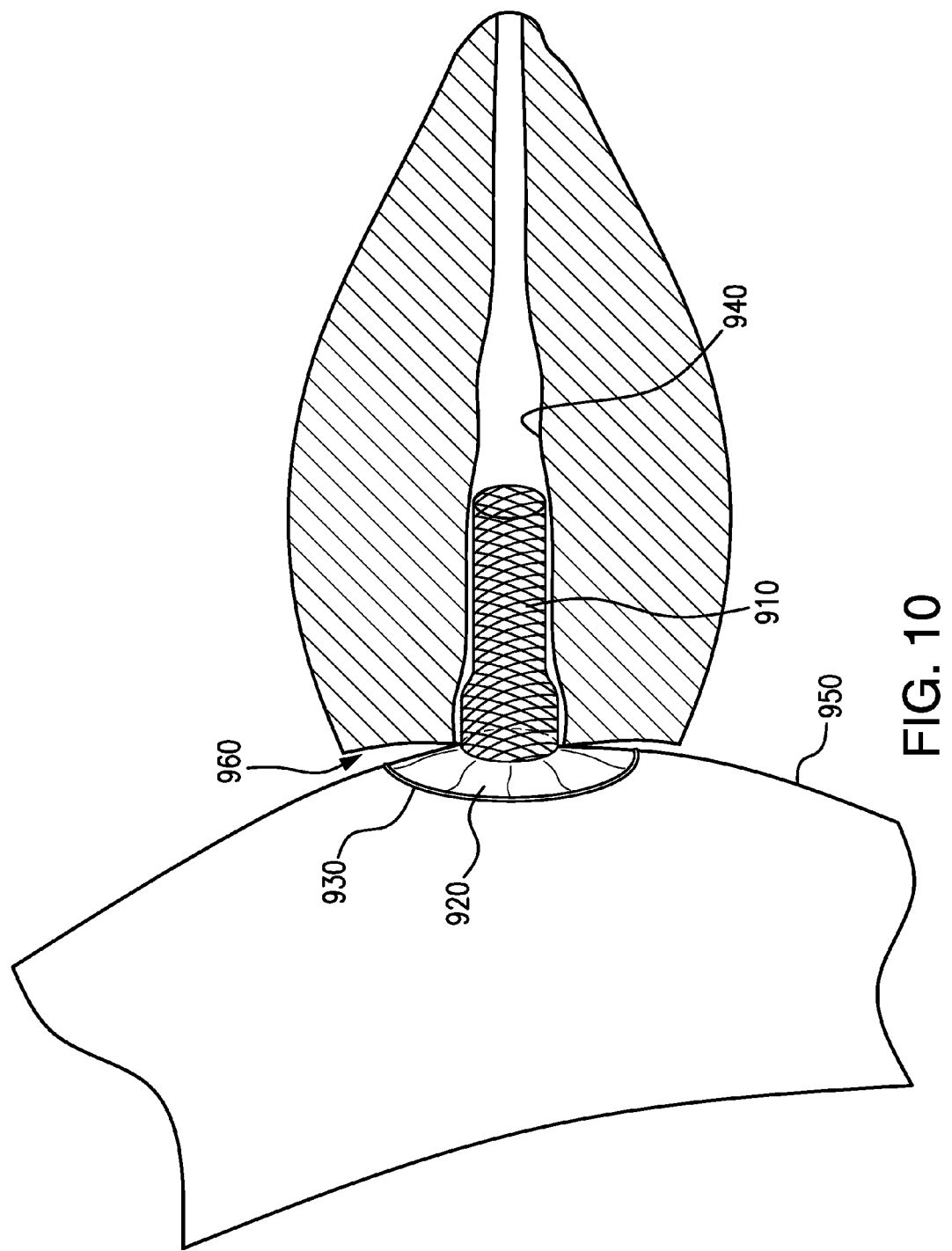
FIG. 10 is a perspective view of the pancreatic device of FIG. 9, illustrating the device implanted within a Whipple operation whereby the pancreatic protective portion is positioned within the pancreatic duct and the small bowel protective portion of the device is positioned within the small bowel with the proximal aspect of the stent protecting a small bowel-pancreatic anastomosis.

With reference now to FIG. 10, the pancreatic/biliary protective device 900 is illustrated as deployed within the pancreatic duct 940 after, for example, Whipple surgery. The stent 910 is deployed within the pancreatic duct 940 traversing the anastomosis 960. The proximal aspect includes or consists of a flexible outer ring 930 approximately 3-4 cm in diameter connected to the stent 910 with an impermeable membrane 920. A loop (not shown) on the outer ring may be used to facilitate endoscopic removal of the device at a later date.

Referring to FIGS. 11 and 12, devices 1000 and 1200 share features in common with the other illustrated examples described above but differ in that they include tapered stents 1030, 1230 that are frustoconical. The stent 1030 is entirely frustoconical, whereas the stent 1230 is frustoconical along only a portion of its length. The stents 1030, 1230 are proximal stents attached to impermeable membranes 1070, 1270 forming tubular linings.

Figure 15:
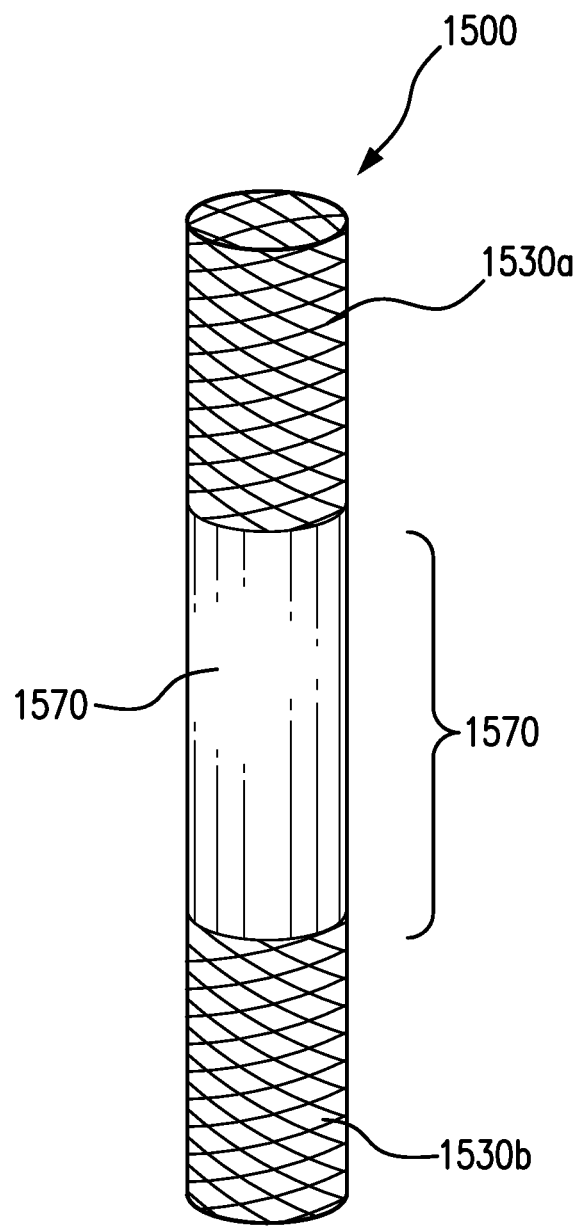

FIGS. 13 to 15 illustrate devices 1300, 1400, and 1500 that share features in common with the other illustrated examples described above, unless indicated otherwise.

Each of the devices 1300, 1400, 1500 includes a proximal stent 1330*a*, 1430*a*, 1530*a* and a distal stent 1330*b*, 1430*b*, 1530*b* separated by an axial spatial gap 1380, 1480, 1580 that is spanned by an impermeable membrane 1370, 1470, 1570 that forms a tubular lining configured to cover and protect an anastomosis as set forth above with regard to other illustrated examples.

The membrane 1370 of device 1300 covers the entire radially outwardly directed surface of the device 1300, whereas the membranes 1480 and 1580 only partially cover the respective radially outwardly directed surfaces of devices 1400, 1500. As illustrated in FIG. 14, the membrane 1470 extends proximally and distally beyond the gap 1480, so that the membrane is partially axially coextensive with each of the stents 1430*a*, 1430*b*. As illustrated in FIG. 15, the membrane 1570 terminates and is joined at respective terminal ends of the stents 1530*a*, 1530*b*, such that the membrane 1570 is axially substantially non-coextensive with stents 1530*a*, 1530*b*. It should be understood that various other arrangements may be provided. For example, proximal and distal stents may be covered to different extents with respect to each other and any combination of features among, e.g., FIGS. 13 to 15 may be provided in any combination.

The impermeable membranes described herein may be impermeable to, inter alia, alimentary tract content such as, for example, bile, water, and/or fecal matter. Further, although the membranes may be described as having at least portions that are not directly radially supported, it should be understood that an underlying support, e.g., a stent structure may be provided along at least one or more portions of the membranes.

Although the rings described in connection with the illustrated embodiments are circular and flexible, it should be understood that the rings may be of any suitable geometry and/or may be rigid.

The methods and systems of the present invention, as described above and shown in the drawings, provide for temporary gastrointestinal tract protection with superior properties including protecting a freshly constructed GI anastomosis, GI staple-line, or the like. While the apparatus and methods of the subject invention have been shown and described with reference to preferred embodiments, those skilled in the art will readily appreciate that change and/or modifications may be made thereto without departing from the spirit and scope of the subject invention. That is, although the present invention has been described with reference to particular examples and embodiments, it should be understood that the present invention is not limited to those examples and embodiments. Moreover, the features of the particular examples and embodiments may be used in any combination. The present invention therefore includes variations from the various examples and embodiments described herein, as will be apparent to one of skill in the art.

What is claimed is:

1. An intraluminal protective device configured to be secured in a lumen of a patient, comprising:
   a proximal tubular stent having opposed proximal and distal end portions and expandable from a collapsed state to an expanded state to exert a first radial force against an interior of the lumen;
   a distal anchor; and
   a tubular lining spanning an axial gap spatially separating the proximal tubular stent from the distal anchor, the tubular lining configured to exert a second radial force on the interior of the lumen along an axial portion of the lumen corresponding to the axial gap, the second radial force being in a range of between (a) zero and (b) less than the first radial force, the tubular lining impermeable to an alimentary tract content;
   wherein the distal anchor includes a distal ring attached to the tubular lining and configured for placement outside of the patient when the proximal tubular stent exerts the first radial force against the interior of the lumen.

2. The device of claim 1, wherein the distal anchor includes a proximal ring configured to exert a third radial force against the interior of the lumen, the third radial force being greater than the second radial force.

3. The device of claim 2, wherein the proximal tubular stent is tapered in shape and has a proximal diameter larger than a distal diameter.

4. The device of claim 2, wherein the second radial force is zero.

5. The device of claim 2, wherein at least one of the first and third radial forces is 2 Newtons or less when the respective proximal or distal tubular stent is compressed to a 25% reduction from a respective resting diameter.

6. The device of claim 2, wherein the tubular lining is configured to traverse a colonic anastomosis with the proximal tubular stent and distal anchor being positioned on respective opposed sides of the colonic anastomosis.

7. The device of claim 2, wherein the tubular lining is configured to cover an entire outer surface of each of the proximal and distal tubular stents.

8. The device of claim 2, wherein a length of the proximal tubular stent is shorter than a length of the distal anchor.

9. The device of claim 1, wherein the distal ring is flexible.

10. The device of claim 1, wherein the second radial force is zero.

11. The device of claim 1, wherein the first radial force is a differential radial force, wherein, by axial length, a proximal 25% of the proximal tubular stent exerts a higher radial force than a distal 75% of the proximal tubular stent.

12. The device of claim 1, wherein the proximal tubular stent is tapered in shape with a proximal diameter larger than a distal diameter.

13. The device of claim 1, wherein the distal ring is configured to be disposed exterior to an anus of the patient when the device is implanted and includes an adjustment mechanism adapted to adjust an axial length of the tubular lining between the distal ring and the proximal tubular stent and an axial length of the gap.

14. The device of claim 1, wherein the tubular lining is adapted to traverse an anal canal of the patient.

15. The device of claim 1, wherein the tubular lining covers an entire outer surface of the proximal tubular stent.

16. The device of claim 1, wherein the distal ring is configured to be disposed on an exterior of the patient and the proximal tubular stent is configured to be disposed in the lumen of a rectum of the patient when the device is implanted.

17. The device of claim 1, wherein the proximal stent is configured to be delivered in a collapsed state through a guide wire under endoscopic visualization.

18. The device of claim 1, wherein the proximal tubular stent is configured, when compressed to a 25% reduction in diameter from a resting diameter, to exert a radial force between 2 Newtons and 3 Newtons at a proximal portion of the proximal tubular stent and a radial force of less than 2 Newtons at a distal portion of the proximal tubular stent.

19. An intraluminal protective device configured to be secured on interior and exterior portions of a patient, comprising:
   a proximal tubular stent having opposed proximal and distal end portions and being expandable from a collapsed state to an expanded state to exert a first radial force against the interior of the lumen;
   a distal anchor including a proximal ring configured for placement within the patient and a distal ring configured for placement on an exterior of the patient; and
   a tubular lining spanning an axial gap separating the proximal tubular stent and the distal anchor, the tubular lining being configured to exert a second radial force on the interior of the lumen at a location along an axial portion of the lumen corresponding to the axial gap, the second radial force being in a range of between (a) zero and (b) less than the first radial force exerted by the proximal tubular stent, the tubular lining substantially impermeable to an alimentary tract content,
   wherein the tubular lining attaches the proximal ring to the proximal tubular stent and wherein the tubular lining attaches the distal ring to the proximal ring.

20. The intraluminal protective device as recited in claim 19, wherein the proximal ring is configured for placement within a rectum of the patient.

21. The intraluminal protective device as recited in claim 19, wherein the distal ring is configured for placement adjacent an anal verge of the patient.

22. The intraluminal protective device as recited in claim 19, further including a loop attached to the proximal ring and configured for transanal removal of the device.

23. The intraluminal protective device as recited in claim 22, wherein the loop is attached on an interior surface of the proximal ring.

24. The intraluminal protective device of claim 22, further comprising a plurality of loops.

25. The intraluminal protective device of claim 19, wherein the distal ring has a diameter greater than a diameter of the proximal ring.

26. The intraluminal protective device of claim 19, wherein a diameter of the distal ring is sufficient to resist entry of the ring into an anus of the patient.

27. The intraluminal device of claim 19, wherein the impermissible barrier connecting the proximate ring and distal ring is configured to be axially compressed for normal functioning of an anal canal of the patient.

28. The intraluminal device of claim 19, wherein the proximal ring is configured to proximally fix the device in an interior of the patient.

29. The intraluminal device of claim 19, wherein the impermissible layer attaching the proximal ring to the distal ring is configured for spanning an anus of the patient from an interior to an exterior of the patient.

30. An intraluminal protective device configured to traverse an anal canal and protect an anastomosis of a patient, comprising:
   a proximal tubular stent having opposed proximal and distal end portions and being expandable from a collapsed state to an expanded state to exert a first radial force against the interior of the lumen;
   a distal anchor including a proximal ring configured for placement within the patient, a distal ring configured for placement on an exterior of the patient, and a loop attached to the proximal ring and configured for transanal removal of the device;
   a tubular lining spanning an axial gap separating the proximal tubular stent and the distal anchor, the tubular lining being configured to exert a second radial force on the interior of the lumen at a location along an axial portion of the lumen corresponding to the axial gap, the second radial force being in a range between (a) zero and (b) less than the first radial force exerted by the proximal tubular stent, the tubular lining substantially impermeable to an alimentary tract content; and
   wherein the tubular lining attaches the proximal ring to the distal ring and is configured to extend from an interior of the patient to an exterior of the patient.

* * * * *